United States Patent [19]

Goldman

[11] Patent Number: 5,429,130
[45] Date of Patent: Jul. 4, 1995

[54] PERCUTANEOUS VASCULAR UNIPOLAR ELECTRICALLY CONDUCTIVE SHEATH

[76] Inventor: Daniel S. Goldman, 140 E 81st St., Apt. 9F, New York, N.Y. 10028

[21] Appl. No.: 17,643

[22] Filed: Feb. 12, 1993

Related U.S. Application Data

[63] Continuation-in-part of Ser. No. 879,201, May 6, 1992, abandoned.

[51] Int. Cl.6 .......................... A61B 5/04; A61N 1/05
[52] U.S. Cl. ........................................ 128/642; 607/122
[58] Field of Search ........................ 128/642; 607/122

[56] References Cited

U.S. PATENT DOCUMENTS

| | | | |
|---|---|---|---|
| 3,087,486 | 4/1963 | Kilpatrick | 128/642 |
| 3,568,660 | 3/1971 | Crites et al. | 607/122 |
| 3,817,241 | 6/1974 | Grausz | 128/642 |

FOREIGN PATENT DOCUMENTS 1937137 2/1970 Germany ........................ 128/642

Primary Examiner—Lee S. Cohen
Attorney, Agent, or Firm—Kane, Dalsimer, Sullivan, Kurucz, Levy, Eisele and Richard

[57] ABSTRACT

This invention is directed towards a unipolar device used in conjunction with a device for measuring or delivering energy through the body in a unipolar configuration.

22 Claims, 4 Drawing Sheets

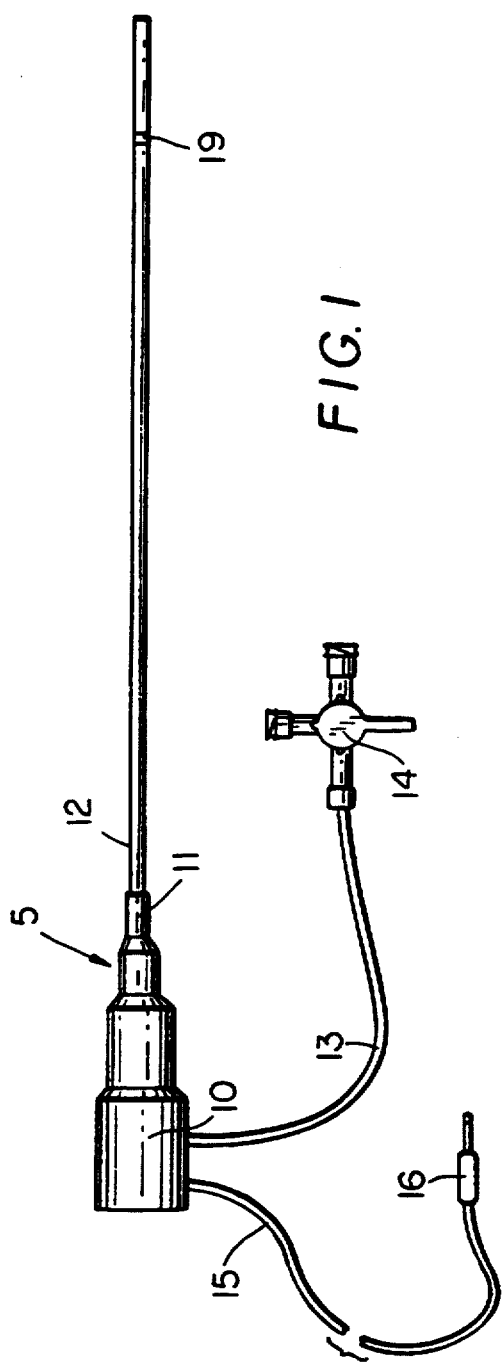
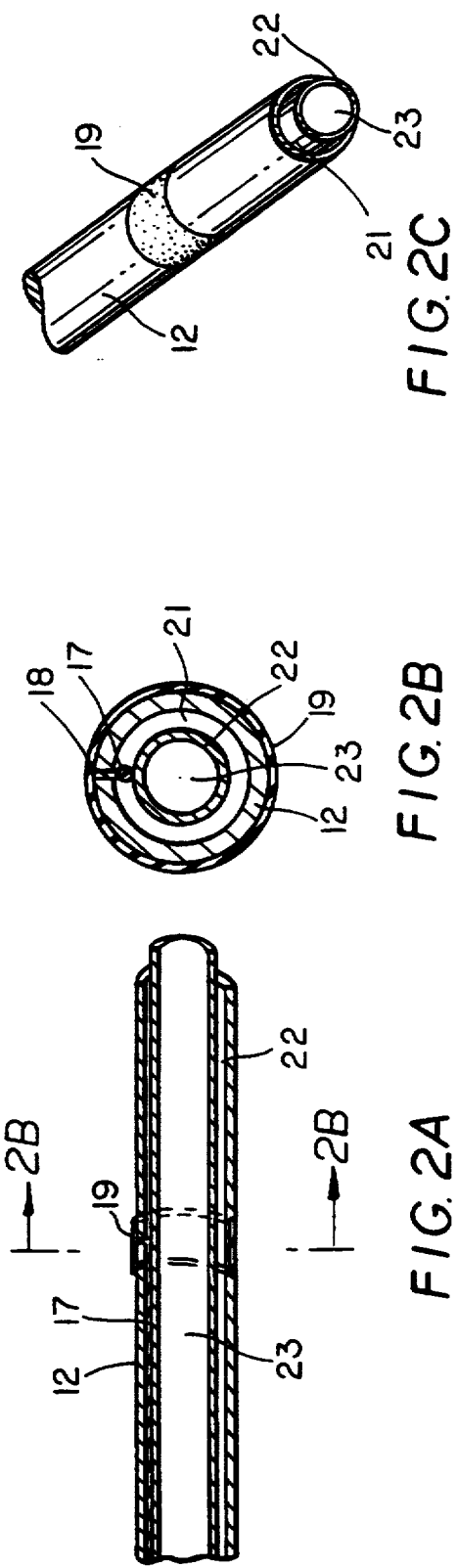

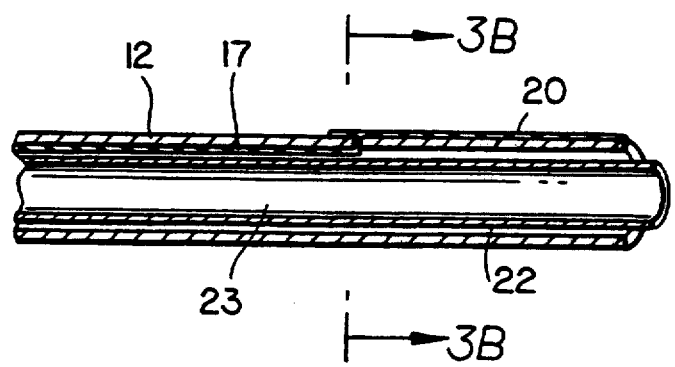
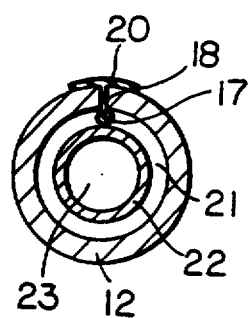
FIG.3A    FIG.3B
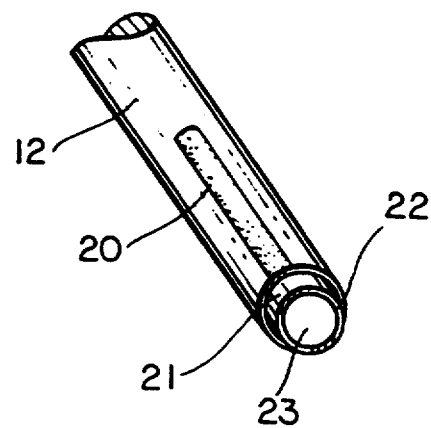
FIG.3C

PERCUTANEOUS VASCULAR UNIPOLAR ELECTRICALLY CONDUCTIVE SHEATH

This application is a continuation-in-part of my Application No. 879,201 filed on May 6, 1992, now abandoned.

FIELD OF THE INVENTION

This invention is directed towards a vascular sheath in a unipolar configuration which facilitates the conduction of electricity between a patient's body and a medical device.

BACKGROUND OF THE INVENTION

This invention is directed towards a vascular sheath in a unipolar configuration which facilitates the conduction of electricity between a patient's body and a medical device. A typical usage of an electrically conductive medical device is as a recording device used to measure the electrical potential occurring during the beating of the heart. In this manner the recording device is used in conjunction with a detecting means, such as electrically conductive electrodes inserted into the patient's body. The electrically conductive electrodes interface with the recording device and provide the means of detecting the electrical impulses of the heart. Electrically conductive electrodes can likewise be used to deliver energy to the heart or other organs, as is the case with catheter ablation, to cite but one example.

In measuring the electrical potential of the heart in delivering electrical energy to the body, a circuit must be established within the body in order to effect a flow of electrical current. It is known in the art to use two electrodes on one catheter, known as a bipolar configuration.

SUMMARY OF THE INVENTION

It is an object of the invention to provide a device used to conduct electricity in a unipolar configuration which provides an electrical conductor to serve as the common connection as well as providing an insulated conduit through which an electrode, dilator, catheter or the like can be inserted.

A further object is to provide an electrically conductive sheath in a unipolar configuration that facilitates the conduction of electricity within the body for medical devices which provide electrical measurements of bodily function or facilitate the delivery of energy to the body.

According to the present invention a unipolar device and method is used with a medical device for measuring or delivering energy in the body. The unipolar configuration provides one pole within the body and provides a conduit in which a second pole can be inserted into the body.

An illustrative example is provided wherein the device is used to measure the electrical potential of the heart. The device includes a sheath forming an elongated tube that is made electrically conductive on its exterior but which is insulated on its interior. The sheath permits an electrically conductive electrode to pass through the sheath. In this manner the interior of the sheath insulates the electrode from the electrically conductive exterior of the sheath. Thus, the unipolar device provides one point of contact. The sheath acts as a conduit for the electrode, which provides a second point of contact to complete an electrical circuit necessary to conduct electricity in the patient's body. The unipolar configuration is an improvement over the bipolar configuration known in the art for the reason that it provides a common ground in a central standard location.

This device may serve as an electrical ground for other current measurements in the body including pH, $pCO_2$, and $Po_2$ and is also suitable for various applications where energy is delivered to the body. Examples of such energy delivery applications include coagulation, electrical surgery, and catheter ablation, and other applications where an indifferent or ground connection are necessary.

BRIEF DESCRIPTION OF THE DRAWINGS

FIG. 1 is a side elevational view of a first embodiment of the present invention.

FIG. 2A is a side perspective view of the first embodiment.

FIG. 2B is a front end view along lines 2B in FIG. 2A.

FIG. 2C is a top perspective view of the first embodiment.

FIG. 3A is a side perspective view of a second embodiment of the present invention.

FIG. 3B is a front end view along lines 3B in FIG. 3A.

FIG. 3C is a top perspective view of the second embodiment.

DETAILED DESCRIPTION OF THE PREFERRED EMBODIMENTS

Figure 4:
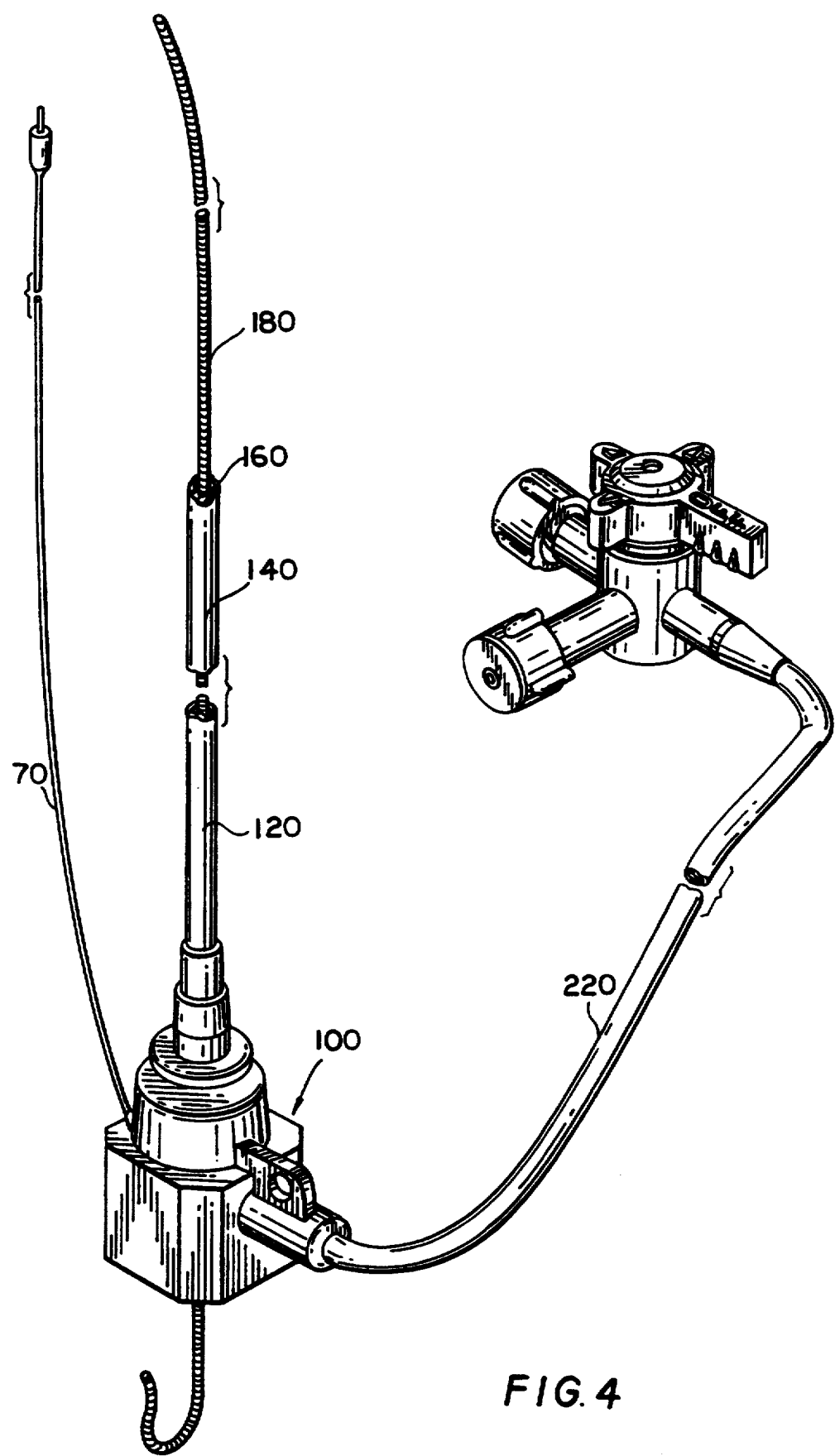
FIG. 4 is a perspective view of a third embodiment of the invention.

Device 5 comprises hemostatic valve housing 10 having strain reliever 11 connecting housing 10 to sheath 12. Connecting tube 13 having three way stop cock 14 is in fluid communication with housing 10, as provided on conventional sheath sets. Housing 10 is provided with electrical connecting lead wire 15 and connecting pin 16 which may be of any length and any connecting pin configuration.

Electrically connecting lead wire 15 and 16 connecting pin are provided in configurations suitable for electrically connecting to a medical device. Such medical devices could be, for example, a device for recording electrical energy within a patient's body or a device for delivering energy to the patient's body. Device 5 is adapted for use in any of these procedures. The term "external circuit" shall be used to describe the kinds of medical devices to which device 5 can be electrically connected.

As best seen in FIG. 2A, sheath 12 envelopes electrode lead wire 17 and inner sheath liner 22. Electrode lead wire 17 is positioned between sheath 12 and inner sheath liner 22. Electrode lead wire 17 is electrically connected to electrical connecting lead wire 15. Channel 23 is formed in the space in inner sheath liner 22 for receipt of dilators, catheters, electrodes, and the like. The inner sheath liner 22 provides for electrical insulation between the ring electrode lead wire 17 and the catheter or body fluids that may be contained within the space in the channel 23.

As best viewed in FIG. 2B the outermost ring electrode 19 is in intimate contact with sheath 12 so that the ring electrode 19 will form a contiguous surface with sheath 12. Electrode lead wire 17 is in electrical contact with the ring electrode 19 where it passes through an aperture (not shown) in sheath 12 by means of perpendicular wire 18. Channel 23 is the central channel through which a dilator, catheter, electrode and the like is placed during insertion of the device percutaneously.

FIG. 2C is an oblique view of the distal aspect of the sheath assembly in FIG. 2. Inner sheath 22 is separated from sheath 12 by space 21. Ring electrode 19 encircles sheath 12 and is in contiguous contact therewith. Ring electrode is depicted as providing a conductive surface over only part of sheath shaft. The ring electrode, or other suitable configuration, could be sized to provide a conductive surface over the entirety of the sheath 12. In other words, the configuration of electrode 19 can be selected to provide a conductive surface over the whole surface or part of the whole surface of sheath 12.

A second embodiment of the invention is shown in FIGS. 3A–3C. Sheath 12 envelopes inner sheath liner 22 and electrode lead wire 17, which is located in the space between sheath 12 and inner sheath liner 22. Electrode lead wire 17 is electrically connected to electrical connecting lead wire 15. Inner sheath liner 22 forms dilator/catheter channel 23. The exterior of sheath 12 is provided with strip electrode 20. The inner sheath liner further provides for electrical insulation between the electrode lead wire 17 and the catheter or body fluids that may be contained within the space in the channel 23.

As viewed in FIG. 3B, strip electrode 20 is in intimate contact with sheath 12 and forms a substantially contiguous surface with sheath 12. Electrode lead wire 17 is electrically connected to strip electrode 20 by means of perpendicular wire 18 that passes through sheath 12 through an aperture (not shown). Channel 23 is the central channel through which a dilator, catheter, electrode and the like is placed during insertion of the device percutaneously. As best viewed in FIG. 3C, sheath 12 is provided on its exterior with strip electrode 20 and inner sheath 22 is separated from sheath 12 by space 21.

FIG. 4 shows the unipolar device 100 of a third embodiment comprising a sheath 120 forming an elongated tube that is electrically conductive on the entirety of its exterior surface 140 but which is insulated on its interior surface 160. The sheath 120 advantageously receives an electrically conductive electrode 180. Since the interior of the sheath 120 insulates the electrode 180 from the electrically conductive exterior 140 of the sheath 120, the unipolar device provides one point of electrical contact and a conduit for a second electrode which completes the electrical circuit necessary to detect the electrical potential of the heart. Sheath 120 should be of a length sufficient to complete the circuit while minimizing noise and interference that could affect the recording of the electrical potential of the heart.

One end of the sheath is provided with a connector 70 which provides means for connecting the device to an electrical circuit (not shown). The connector consists of a single conductor insulated wire connected to a plug (tip jack or banana plug are available options). In addition, there is a side arm sheath (hollow tube) 220 for flushing and optional fluid administration through the sheath.

Figure 5:
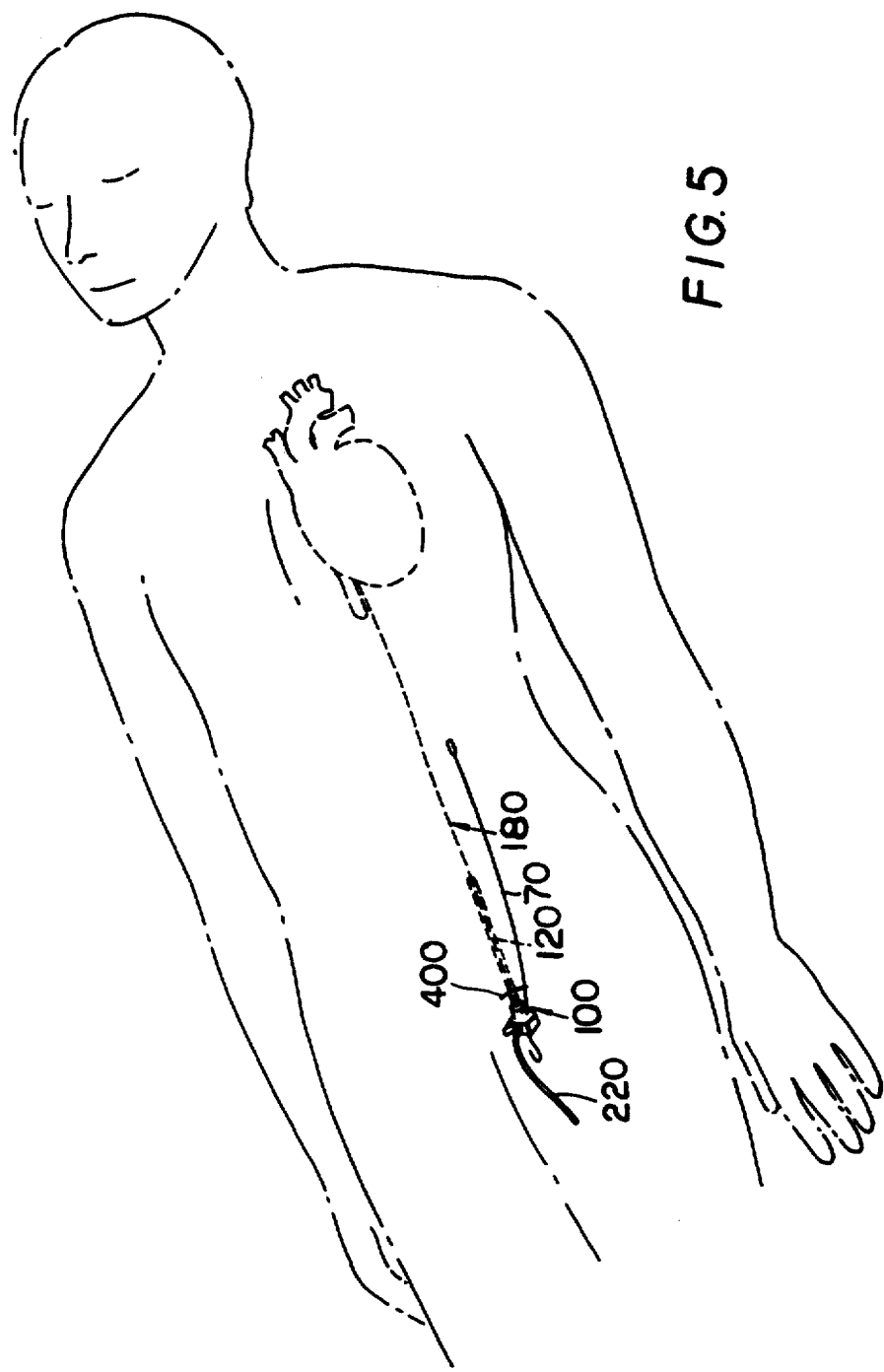
FIG. 5 depicts a method for using the embodiments of this invention.

FIG. 5 depicts a method for using the unipolar device wherein the device is used in the recording of and measuring of the electrical potential of the heart. A puncture 40 is made in the patient and sheath 120 is inserted inside the incision. In FIG. 5, the puncture 40 is made in the groin area, but persons skilled in the art would realize that it could be made at any other location that is suitable. An electrode 180 is inserted through the sheath so that both the sheath 120 and the electrode 180 are within the patient's body. The electrically conductive electrode is moved manually through the sheath and up through the patient's abdomen and thorax until it is in contact with the heart. Connector 150 provides means for connecting the device to a recording apparatus for measuring the electrical potential of the heart (not shown). Since two electrical contacts are provided by the electrode 180 and exterior of the sheath 120, an electrical circuit is completed and permits the electrical potential of the heart to be measured on the recorder.

I claim:

1. A percutaneous vascular unipolar electrically conductive device for insertion into a patient's vascular system, comprised of:

an elongated intravascular sheath having an axial channel, an outer coaxial surface and an inner coaxial surface;

an electrically conductive area located upon at least a portion of the outer coaxial surface of the sheath for direct electrical body contact upon insertion into the patient's vascular system;

said axial channel of the elongated vascular sheath being sized and shaped to slidably receive therethrough a catheter having an electrode;

an insulator on the sheath for electrically isolating the electrically conductive area on the outer coaxial surface of the sheath from the electrode of the catheter when same is slidably received within the axial channel; and a conductor that is electrically connected to the electrically conductive area and is adapted to be connected to an external circuit to provide an indifferent, ground connection for an electrical circuit passing through the patient's body between the catheter electrode and the electrically conductive area of the sheath.

2. The device as set forth in claim 1 wherein the entire outer surface of the sheath constitutes the electrically conductive area.

3. The device as set forth in claim 1 wherein the electrically conductive area is a ring about the outer surface of the elongated sheath.

4. The device as set forth in claim 1 wherein the electrically conductive area is a strip upon the outer surface of the elongated sheath.

5. The device as set forth in claim 1 wherein a catheter having an electrode is disposed within the axial channel of the elongated intravascular sheath.

6. The device as set forth in claim 1 wherein the conductor that connects the electrically conductive area to an external circuit is a conductor wire articulated at a first end to the sheath and articulated at a second end to a plug for interfacing with an external circuit.

7. The device as set forth in claim 1 further including a connecting tube operatively connected to said elongated sheath, said connecting tube having a three way stop cock.

8. The device as set forth in claim 1 further including an inner sheath within said elongated intravascular sheath, and wherein said conductor includes a lead wire positioned between the elongated intravascular sheath and the inner sheath and connected to the electrically conductive area.

9. The device as set forth in claim 8 wherein the electrically conductive area is a ring about the outer surface of the elongated sheath.

10. The device as set forth in claim 8 wherein the electrically conductive area is a strip upon the outer surface of the elongated sheath.

11. The device as set forth in claim 8 wherein a catheter having an electrode is disposed within the axial channel of the elongated intravascular sheath.

12. The device as set forth in claim 8 wherein the conductor that connects the electrically conductive area to an electrical circuit is a conductor wire articulated at a first end to the sheath and articulated at a second end to a plug for interfacing with an external circuit.

13. The device as set forth in claim 8, further including a connecting tube having a three way stop cock, said connecting tube being in fluid communication with the elongated sheath.

14. A method of utilizing the device of claim 1 for detecting the electrical potential of a patient's heart comprising the steps of:
   a) making a single puncture in a patient;
   b) inserting the elongated intravascular sheath through the puncture and into the patient's vascular system, the electrically conductive area serving as a common ground connection;
   c) inserting a catheter having an electrode through the elongated intravascular sheath so the electrode is in contact with the patient's heart; and
   d) connecting the catheter electrode and ground to a recording device to detect the electrode potential of the patient's heart.

15. A percutaneous vascular unipolar electrically conductive device for conducting electricity within a patient's body comprised of:
   an elongated sheath having an axial channel and an outer coaxial surface and an inner coaxial surface;
   an electrically conductive area located upon at least a portion of the outer coaxial surface of the sheath such that the entire outer surface of the elongated sheath constitutes the electrically conductive area;
   an inner sheath for electrically isolating the channel from the electrically conductive area on the outer coaxial surface of the sheath, said inner sheath being within said elongated sheath, a lead wire positioned between the elongated sheath and the inner sheath, the lead wire being in electrical communication with the electrically conductive area; and
   means for connecting the lead wire to an external circuit.

16. A percutaneous vascular unipolar electrically conductive device for insertion into a patient's vascular system, comprised of:
   a first sheath having an axial channel, an outer coaxial surface and an inner coaxial surface;
   an electrically conductive area located at least upon a portion of the outer coaxial surface of the first sheath for direct electrical body contact upon insertion into the patient's vascular system;
   a second sheath having an axial channel and an outer coaxial surface and an inner coaxial surface located interior of the first sheath, said axial channel of the second sheath being sized and shaped to slidably receive therethrough an electrode catheter;
   a lead wire positioned between the first sheath and the second sheath and electrically connected to the electrically conductive area;
   a conductor wire articulated at a first end to the first sheath and being in electrical body contact upon insertion into the patient's body and articulated at a second end to a plug for connecting the electrically conductive area to an external circuit to provide an indifferent, ground connection for an electrical circuit passing through the patient's body between the electrode catheter and the electrically conductive area.

17. The device as set forth in claim 16 wherein a portion of the outer surface of the first sheath constitutes the electrically conductive area.

18. The device as set forth in claim 16 wherein the electrically conductive area is a ring about the first sheath.

19. The device as set forth in claim 16 wherein the electrically conductive area is a strip upon the exterior of the first sheath.

20. The device as set forth in claim 16 wherein an electrode catheter is disposed within the channel of the second sheath.

21. A method of utilizing the device of claim 16 for detecting the electrical potential of a patient's heart comprising the steps of:
   a) making a single puncture in a patient;
   b) inserting the device through the puncture and into the patient's vascular system, the electrically conductive area serving as a common ground connection;
   c) inserting an electrode catheter through the second sheath so the electrode is in contact with the patient's heart; and
   d) connecting the catheter electrode and ground to a recording device to detect the electrical potential of the patient's heart.

22. A percutaneous vascular unipolar electrically conductive device for conducting electricity within a patient's body comprised of:
   a first sheath having an axial channel and an outer coaxial surface and an inner coaxial surface;
   an electrically conductive area located upon substantially the entire outer surface of the first sheath;
   second sheath having an axial channel and an outer coaxial surface and an inner coaxial surface located interior of the first sheath;
   a lead wire positioned between the first sheath and the second sheath and electrically connected to the electrically conductive area;
   a conductor wire articulated at a first end to the first sheath and being in electrical body contact upon insertion into the patient's body and articulated at a second end to a plug for connecting the electrically conductive area to an external circuit.

* * * * *